United States Patent [19]

Yurek et al.

[11] Patent Number: 5,662,703
[45] Date of Patent: Sep. 2, 1997

[54] ROLLING MEMBRANE STENT DELIVERY DEVICE

[75] Inventors: Matthew T. Yurek, Bloomington; Richard S. Kusleika, Eden Prairie, both of Minn.

[73] Assignee: Schneider (USA) Inc., Plymouth, Minn.

[21] Appl. No.: 716,052

[22] Filed: Sep. 19, 1996

Related U.S. Application Data

[63] Continuation-in-part of Ser. No. 421,960, Apr. 14, 1995, abandoned.
[51] Int. Cl.⁶ ........................................... A61F 2/06
[52] U.S. Cl. ................... 623/1; 623/12; 606/194; 606/195
[58] Field of Search ............... 623/1, 12; 606/194, 606/195; 604/271

[56] References Cited

U.S. PATENT DOCUMENTS

| 4,655,771 | 4/1987 | Wallsten . |
| 4,732,152 | 3/1988 | Wallsten et al. . |
| 4,848,343 | 7/1989 | Wallstén et al. ............ 128/343 |
| 5,180,362 | 1/1993 | Worst . |
| 5,224,953 | 7/1993 | Morgentaler . |

FOREIGN PATENT DOCUMENTS

| 0 554 579 A1 | 8/1993 | European Pat. Off. . |
| WO93/22986 | 11/1993 | WIPO . |
| WO94/15549 | 7/1994 | WIPO . |

OTHER PUBLICATIONS

PCT International Search Report in corresponding PCT application No. PCT/IB96/00146, filed Feb. 26, 1996, with 2-page Annex.

Primary Examiner—Paul B. Prebilic
Attorney, Agent, or Firm—Haugen and Nikolai, P.A.

[57] ABSTRACT

A device for deploying radially self-expanded stents and other radially expandable stents includes an inner catheter, an outer catheter surrounding the inner catheter, and a tubular stent retaining sheath formed of a rolling membrane. The sheath is doubled over upon itself to provide an inner sheath layer attached to the inner catheter, and an outer sheath layer attached to the outer catheter. The sheath layers extend along and surround a radially self-expanding stent, to maintain the stent distally of the inner catheter and in a radially compressed, axially elongated state. Distally of the stent, the inner and outer sheath layers converge and are narrowed in the distal direction to define a tapered distal tip. To release the stent, the outer catheter is moved proximally to roll the membrane away from its surrounding relation to the stent, whereupon the stent radially self-expands progressively, beginning at its distal end. When completely retracted after stent release, the sheath surrounds a distal region of the inner catheter, and can provide a protective layer between arterial tissue and a dilatation balloon supported along the distal region. As an alternative, a stent formed of a recovery metal can be plastically deformed into a reduced radius state for delivery, which facilitates use of a more flexible stent retaining sheath. A further alternative involves securing the sheath proximally of the dilatation balloon, so that sheath retraction leaves the dilatation balloon exposed, rather than covered by the sheath.

54 Claims, 4 Drawing Sheets

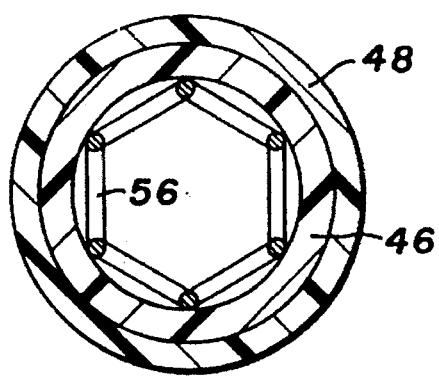
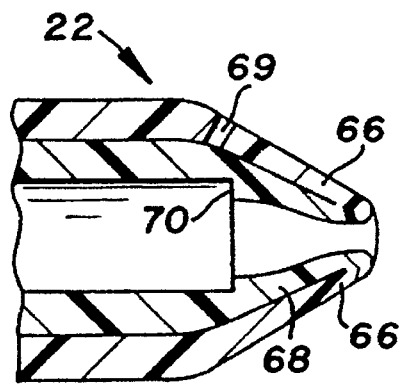
FIG.4   FIG.5
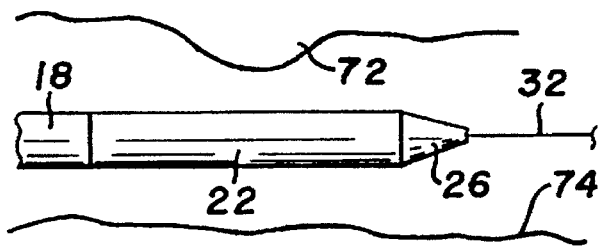
FIG.6
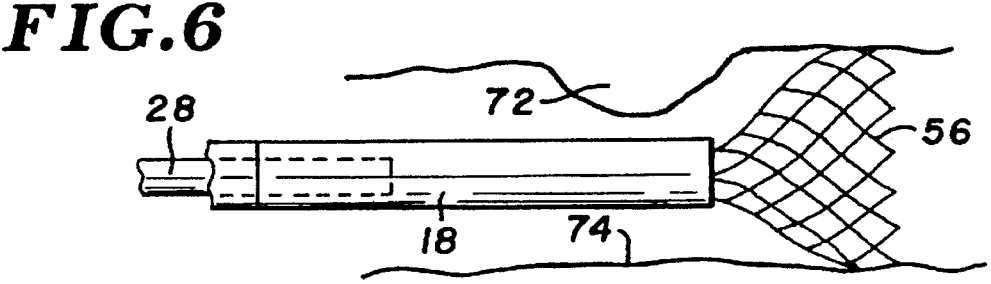
FIG.7
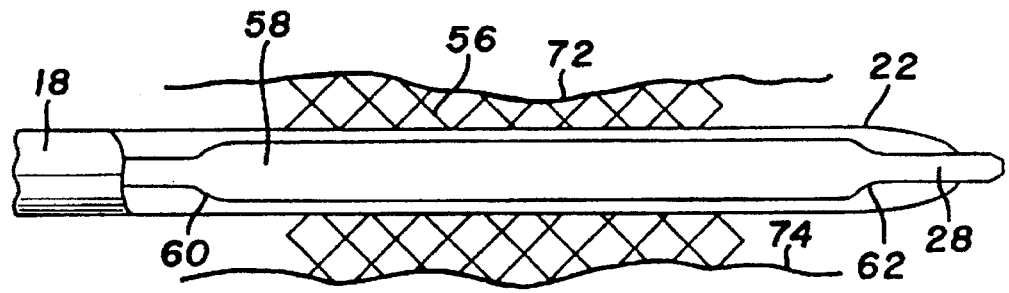
FIG.8

ROLLING MEMBRANE STENT DELIVERY DEVICE

This is a continuation of application Ser. No. 08/421,960, filed on Apr. 14, 1995 now abandoned.

BACKGROUND OF THE INVENTION

The present invention relates to devices for deploying body implantable prosthesis intended for fixation in body lumens, and more particularly to the delivery and placement of radially self-expanding stents or other radially expandable stents.

Certain prosthesis known as radially self-expanding stents are useful in a variety of patient treatment and diagnostic procedures, for fixation in blood vessels, biliary ducts and other lumens to maintain the passages. A highly preferred construction for a radially self-expanding stent is a flexible tubular braided structure formed of helically wound thread elements, as disclosed in U.S. Pat. No. 4,655,771 (Wallsten). Wallsten teaches use of a catheter for delivering the stent to the intended treatment site. A pair of grips maintain the stent at the distal end of the catheter and are controlled by an operational member at the proximal end of the catheter to release the stent after positioning and initial medial stent self-expansion.

Another approach to deploying self-expanding stents is shown in U.S. Pat. No. 4,732,152 (Wallsten et al) and in U.S. Pat. No. 4,848,343 (Wallsten et al). Often referred to as the "rolling membrane" method, this approach utilizes a tubular membrane folded over upon itself to provide a double wall for maintaining a self-expanding stent at the distal end of the catheter. The outer wall of the membrane is movable proximally to expose the stent and allow a radial self-expansion, beginning at the distal end of the stent. More particularly, one end of the membrane is attached to an inner catheter or probe, and the other end of the membrane is connected to an outer catheter that surrounds the probe. When the outer catheter is moved proximally relative to the inner catheter, it moves the outer wall of the membrane proximally as well, to expose the stent and allow radial self-expansion.

Yet another approach is shown in PCT patent application, Publication No. WO 94/15549 entitled "Method for Deploying Body Implantable Stent". This application describes several stent deployment devices employing interior and exterior catheters to deploy prostheses including radially self-expanding stents. One of these versions (FIGS. 9–13) employs a rolling membrane controlled through manipulation of the catheters to release a stent for self-expansion.

Stents constructed of a recovery metal, e.g. an alloy of titanium and nickel such as that sold under the brand name Nitenol, can be used in lieu of radially self-expanding stents for certain applications. A recovery metal stent may be formed initially in an expanded radius configuration, then plastically deformed while cool into a reduced radius configuration for delivery to a treatment site. Following delivery the stent is heated, which causes it to radially expand toward its original radius and into contact with tissue at the treatment site. Devices for delivering recovery metal stents and radially self-expanding stents can be constructed according to the same general principles.

While quite effective in certain applications, these devices generally incorporate interior catheters, probes or other members surrounded by the stent being deployed, and generally rely on a relatively rigid outer member, usually an exterior catheter, to surround and maintain the stent under radial compression. Such devices may be too large for deploying stents within narrower blood vessels and other body passages, and may be difficult to maneuver distally through serpentine passages defined by the body lumens.

Frequently during a procedure involving stent deployment, it is desired to force the stent against surrounding tissue after its deployment. This insures a more secure positioning of the stent, a more uniform lumen for fluid flow, and also more reliably establishes a final axial length (i.e. degree of axial contraction) of the stent. It is important during lesion treatment procedures to determine the final length (or degree of axial contraction) of the stent after self-expansion, to insure that a given stent is of sufficient length in relation to the lesion being treated. A dilatation balloon, mounted near the distal end of the catheter, can be used for this purpose. When using such a balloon, it would be desirable to provide protection against accidental bursting of the balloon either during or after its inflation.

Therefore, it is an object of the present invention to provide a device for deploying radially self-expanding stents, with sufficient axial rigidity yet enhanced flexibility for accommodating advancement through narrow and non-linear body passages.

Another object is to provide a reduced diameter stent retaining tip for a stent deployment catheter.

A further object is to provide a stent delivery apparatus that affords good axial stiffness and trying characteristics, whether steered through body passages or advanced over a guidewire.

Yet another object is to provide a device for delivering a radially self-expanding stent with a dilatation balloon expandable against the delivered stent to force it against surrounding tissue, and further incorporating a fluid tight membrane surrounding the dilatation balloon to afford added protection during high pressure dilatation procedures.

SUMMARY OF THE INVENTION

To achieve these and other objects, there is provided a device for deploying an expandable stent at a treatment site within a body. The device includes a first (or inner) catheter and a stent retaining member. The member is disposed at the distal end region of first catheter and includes an inner layer extending distally beyond the first catheter. The member is turned back upon itself to form an outer layer extended toward the first catheter. The inner layer is adapted to retain an expandable stent in a reduced state along its axial length, with the stent located distally of the first catheter. A means is operable to displace the outer layer relative to the first catheter after delivery, to remove the member from its retaining relation to the stent, to release the stent for expansion at the treatment site.

Preferably the retaining member is a sheath or rolling membrane that surrounds the stent to retain the stent in the reduced state. The preferred sheath comprises a tubular rolling membrane. Because the stent is maintained distally of the catheter rather than surrounding the catheter, it can be delivered at a diameter less than that of the catheter. The inner layer preferably has an inside diameter no larger than the outside diameter of the first catheter. When the stent is radially self-expanding, the inner layer alone (or a combination of the inner and outer layers) retains the stent in a radially compressed, axially elongated state.

The compressed stent and sheath cooperate with one another to provide an improved distal tip for the catheter. In addition to the reduced diameter, the compressed stent and membrane provide a highly favorable combination of axial rigidity and compliance of the tip in bending to accommodate tortuous passageways in blood vessels and other body lumens.

Further improvement is realized by shaping the sheath to form a tapered distal tip. This is accomplished by forming the sheath so that the inner and outer layers, near the point at which the sheath is turned back upon itself, converge in the distal direction. If desired, axial filaments or other stiffening can be provided along the sheath.

Release of the stent involves retracting the sheath, i.e. moving the outer sheath layer proximally to progressively peel or roll the sheath membrane away from the stent. Preferably this is accomplished with a second or outer catheter that surrounds the first catheter and is attached at its distal end to the sheath outer layer. The sheath is rolled by moving the outer catheter proximally relative to the first (inner) catheter. Release is enhanced by a fluid tight construction of the membrane that facilitates introduction of a fluid under pressure between the inner and outer layers. Alternatively, selection of low friction membrane material, or application of low friction coatings to the membrane between the inner and outer sheath layers, can allow the rolling membrane to be withdrawn without applying pressure between the layers.

According to another aspect of the invention, a dilatation balloon is provided near the distal tip of the catheter. The sheath has sufficient length in its inner and outer layers combined, to exceed the axial distance from the catheter distal tip to a proximal end of the dilatation balloon. Consequently, the sheath after retraction extends proximally along the catheter from the distal tip, in surrounding relation to the balloon along the full length of the balloon. So arranged, the sheath provides a layer of protection particularly useful during high pressure angioplasty procedures. Were the dilatation balloon to burst, the dilatation fluid would tend to flow proximally along the sheath and catheter and remain inside of the sheath. Thus, the sheath protects arterial or other tissue against the risk of exposure, to exploding or jetting balloon dilatation fluid. The sheath also prevents any resultant fragments of balloon material from escaping into the bloodstream.

A highly preferred device employs an exterior catheter with a lumen containing an interior catheter, with opposite ends of the sheath secured to the respective catheters and with the sheath inner and outer layers extending distally of both catheters. The outer catheter provides a reliable means for proximally pulling the outer sheath layer to release the stent. Fluids can be provided to the region between the sheath layers via a lumen of the exterior catheter. The sheath alone retains the stent, for a smaller diameter and more maneuverable yet axially rigid deployment device. When the sheath is retracted or proximally withdrawn, the distal end of the inner catheter becomes the distal tip of the device. The sheath overlies and surrounds a dilatation balloon to protect tissue from exposure to jetting balloon dilatation fluid in the event of a balloon rupture during an angioplasty procedure.

IN THE DRAWINGS

For a further appreciation of the above and other advantages, reference is made to the following detailed description and to the drawings, in which:

FIG. 4 is a sectional view taken along the line 4—4 in FIG. 1;

FIG. 5 is a further enlarged view of the device distal end;

FIGS. 6-9 are schematic views illustrating use of the device to deploy a radially self-expanding stent;

DETAILED DESCRIPTION OF THE PREFERRED EMBODIMENTS

Figure 1:
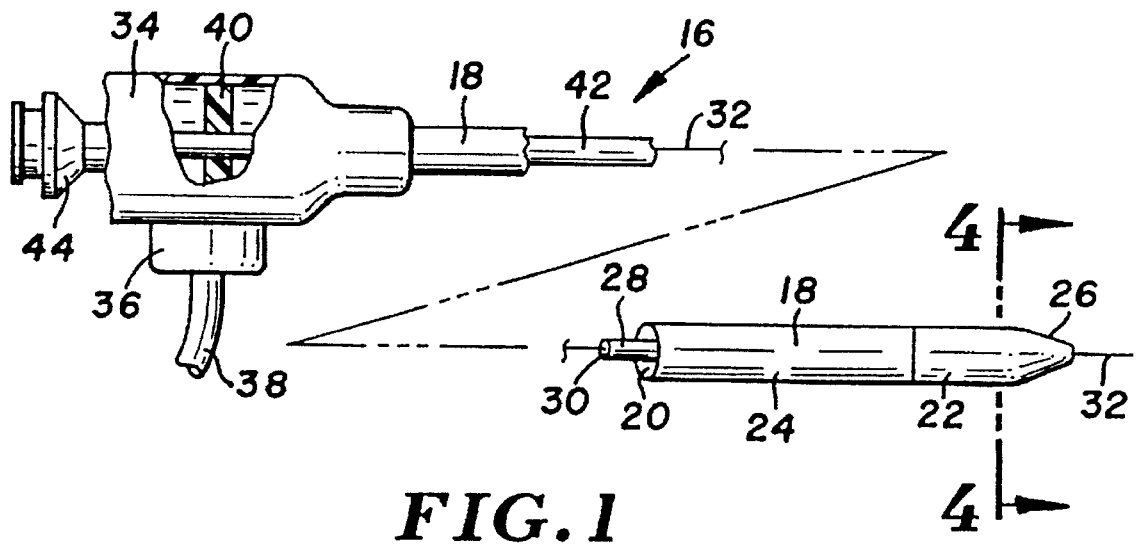
FIG. 1 is an elevation of a device for delivering and deploying a radially self-expanding stent in accordance with the present invention.

Turning now to the drawings, there is shown in FIG. 1 a deployment device 16 for delivering a prosthesis, in particular a radially self-expanding stent, to an intended treatment location within a body lumen such as an artery. After delivering the stent, deployment device 16 is manipulated to controllably release the stent for radial self-expansion to a fixation site within the lumen. Following deployment, a balloon mounted on the device is expanded to force the stent radially outward against surrounding tissue, to more reliably establish a final stent position and axial length.

Deployment device 16 includes an elongate and flexible outer catheter 18 constructed of a biocompatible thermoplastic elastomer, e.g. polyurethane or nylon. The outside diameter of the catheter typically is in the range of 2-42 Fr. (0.7-14 mm). The preferred catheter diameter depends largely on the intended use. For example, the preferred range for coronary applications is about 2-7 Fr. (0.7-2.3 mm), with peripheral applications calling for diameters of about 2-12 Fr. (0.7-4 mm). For abdominal aortic aneurysm, esophageal and tracheal applications, a more preferred range is 7-42 Fr. (2.3-14 mm). Outer catheter 18 has a lumen 20 that runs the length of the catheter.

A tubular sheath 22 is mounted to the distal end 24 of catheter 18. Sheath 22 extends distally beyond the catheter and is shaped to provide a distally converging tip 26. A portion of the outer catheter is broken away to reveal an elongate and flexible inner catheter 28 contained within lumen 20. The inner catheter can be constructed of similar materials employed to form the outer catheter. Inner catheter 28 has a lumen 30 running the catheter length, for containing a guidewire 32, shown to extend distally beyond tip 26.

At its proximal end, outer catheter 18 is mounted to a valve 34. The valve includes a port 36 for receiving fluids supplied via an extension tube 38. Such fluids proceed through the valve to lumen 30, then to the region about tip 26. A portion of valve 34 is removed to reveal an internal sealing gasket 40 that supports an elongate stainless steel tube 42 to guide axial movement of the valve. The stainless steel tube extends distally of the valve into lumen 20 of the outer catheter, and its distal end is joined to the proximal region of inner catheter 28. The stainless steel tube can extend from 10 mm to 200 mm distally along lumen 20, advantageously increasing the axial rigidity of device 16. Steel tube 42 can be perforated or formed as a coil near the distal end of the catheter to enhance its bending flexibility.

Catheters 18 and 28 can be moved axially relative to one another by hand manipulation to move valve 34 relative to steel tube 42. A hub 44 is bonded at the proximal end of stainless steel tube 42. For example, moving the valve proximally while maintaining the steel tube fixed retracts the outer catheter, i.e. moves catheter 18 in the proximal axial direction relative to inner catheter 28.

Figure 2:
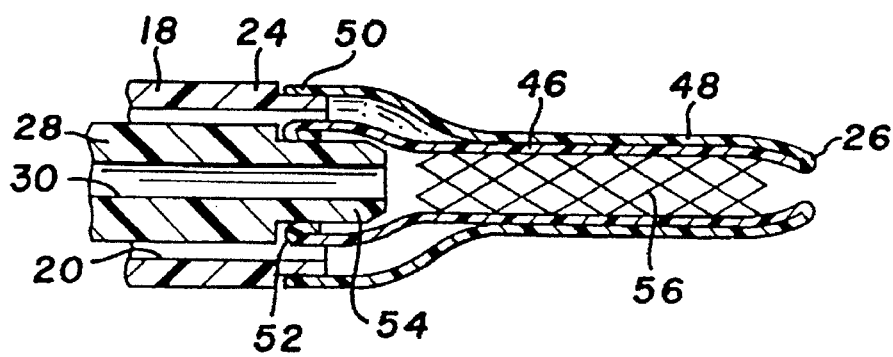
FIGS. 2 and 3 are enlarged sectional views of portions of FIG. 1.

Sheath 22, often referred to as a rolling membrane, is pliable and flexible, and constructed of a suitable body compatible thermoplastic elastomer such as polyurethane. Polyethylene, nylon and their copolymers also may be employed. As best seen in FIG. 2, sheath 22 is doubled over upon itself to form an inner sheath layer 46 and an adjacent outer layer 48, both of which are tubular. Sheath 22 is formed so that both layers 46 and 48 converge in the distal axial direction along tip 26. A proximal end 50 of the outer layer is mounted to the distal end 24 of outer catheter 18, in an annular, fluid tight joint. An opposite end of the sheath, i.e. a proximal end 52 of the inner layer, is attached in similar fashion to the distal end 54 of inner catheter 28. Along most of its length, sheath 22 extends axially such that its wall, in particular inner layer 46, defines an extension of guidewire lumen 30. At the distal tip is an opening of reduced size, yet sufficient to admit guidewire 32 and provide a transition zone from the guidewire to the constrained stent.

A radially self-expanding stent 56 is contained by sheath 22, entirely distally of inner catheter 28. Stent 56 has an open mesh or weave construction, formed of helically wound and braided filaments or perforated tubing of a resilient material, e.g. a body compatible metal such as stainless steel or a titanium nickel alloy. The stent also can be formed of a resilient polymer such as polypropylene or polyethylene. As shown in FIG. 2, stent 56 is elastically deformed into a delivery configuration that reduces its radius and increases its axial length as compared to its normal shape when not subject to external stress. Inner and outer layers 46 and 48 surround the stent and cooperate to maintain it in the delivery configuration.

When stent 56 is radially compressed as shown, its elastic restoring force is applied radially against sheath layers 46 and 48. These sheath layers expand in response to the force of stent 56, until a restoring force in the layers counterbalances the stent restoring force. Sheath expansion is preferably virtually negligible.

As an alternative, the stent can be formed of a recovery metal, such as the nickel titanium alloy sold under the brand name Nitenol. Such stent is plastically deformable, so long as it remains sufficiently cool, into a reduced radius delivery configuration. While cool (e.g. at or below ambient temperature), the stent tends to remain in the reduced radius state. Consequently the surrounding sheath can have greater elasticity if desired, since the sheath need not counteract an elastic restoring force of the stent.

When the recovery metal stent is delivered and positioned at the treatment site, it is heated, which causes the stent to radially expand toward its original, larger radius state, and into intimate contact with tissue at the treatment site once the surrounding sheath has been retracted.

Sheath 22 is retractable by moving outer layer 48 proximally relative to inner layer 46. A hydrophilic material, e.g. polyvinyl pryoladone, is applied to sheath 22 along the outer surface of inner layer 46 and the inner surface of outer layer 48. Silicone or other lubricants also may be used. A liquid lubricant and priming fluid can be provided between the sheath layers, via lumen 20. The coating and lubricant facilitate sliding of the inner and outer layers relative to one another during retraction.

As best seen in FIG. 5, sheath 22 is specially shaped in the region of the distal tip. More particularly, a distal region 66 of the outer layer and a distal region 68 of the inner layer are tapered to converge in the distal direction. Thus, not only does the tip profile converge; its thickness, as well, diminishes in the distal direction. Regions 66 and 68 further provide a transition region over which sheath 22 is treated to substantially alter its hardness. More particularly, sheath 22 and constrained stent 56 over the majority of their length are relatively rigid. Over the transition region, hardness diminishes steadily and considerably to a soft distal end of the tip. More particularly, the durometer of the distal end (Shore Hardness Test) is within a range of 20 D–55 D, and more preferably is about 90 A. Further, an annular feature 70 is formed into the sheath along inner layer 46, to provide a better transition from the relatively rigid stent constraining region to the soft distal end.

A micropore 69 is formed through outer layer 48 to allow egress of liquids from between sheath layers 46 and 48. If desired, the micropore diameter can be selected for maintaining liquids between the sheath layers at a predetermined pressure. A typical diameter for micropore 69 is about 0.001 inches (0.0254 mm). Depending on the application, the micropore diameter may range from about 0.0005 to 0.12 inches (0.0127–3 mm).

With sheath 22 in the stent retaining state as shown in FIG. 2, the distal region along the stent can conform to serpentine arterial passages as device 16 is advanced over guidewire 32 to the intended treatment site. The soft tip and transition regions 66 and 68 reduce the risk of damage to arterial walls or other tissue as the device is advanced.

Figure 3:
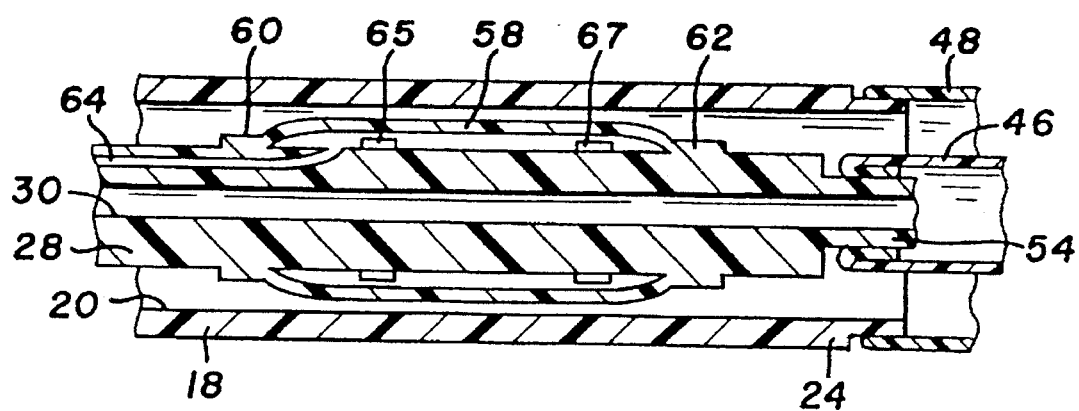

Proximally of distal end 54 (FIG. 3), a dilatation balloon 58 is secured to the inner catheter in fluid tight fashion at a proximal neck 60 and a distal neck 62. A balloon inflation lumen 64 is formed in the inner catheter, and is open to the interior of balloon 58, whereby a balloon inflation fluid can be provided under pressure to radially expand balloon 58. Radiopaque markers 65 and 67 can be used to fluoroscopically indicate the balloon location.

In using device 16 to position and fix stent 56, the initial step is to position guidewire 32 within the patient's body using a guide cannula (not illustrated). This leaves guidewire 32 in place along an artery or other lumen, with a proximal portion of the guidewire outside of the patient. Deployment device 16 is advanced over the guidewire beginning at the proximal portion, with the guidewire being received into guidewire lumen 30. The physician or other user continues to advance device 16 until the distal end region, including stent 56, is positioned at the treatment site, e.g. a lesion 72 along an artery 74 (FIG. 6). Preferably distal tip 26 is beyond lesion 72. Stent 56, still maintained within the sheath, is axially aligned with the lesion. Sheath 22 remains in the stent retaining state.

With device 16 thus positioned, the physician maintains stainless steel tube 42 substantially fixed while moving valve 34 in the proximal direction. This moves outer catheter 18 proximally relative to the inner catheter, drawing outer sheath layer 48 proximally as well. This also proximally moves tip 26, i.e. the location at which sheath 22 is turned back upon itself. Meanwhile, inner catheter 28 abuts stent 56 to prevent any substantial proximal migration of the stent. Consequently the membrane is rolled or peeled from its surrounding relation to the stent, allowing the stent to radially self-expand progressively, beginning at its distal end (FIG. 7).

Continued retraction of sheath 22 results in complete stent release (FIG. 8). Stent 56 has radially self-expanded to a diameter up to 30 times the diameter of outer catheter 18. When sheath 22 is fully retracted, the distal end of the inner catheter becomes the distal tip of the device. Then, device 16 is advanced distally to axially align balloon 58 within stent 56. Following this alignment, fluid under pressure is supplied to balloon 58 via balloon inflation lumen 64, to expand the balloon against stent 56. The pressure from dilatation balloon 58 achieves several beneficial results. First, stent 56 is radially pressed into a more firm engagement with surrounding tissue of the arterial wall, to reduce the risk of stent migration and facilitate more laminar blood flow. Secondly, the added radial expansion is accompanied by an axial shortening of the stent, to more closely approximate a final stent axial dimension that otherwise might occur over a longer period of time (approximately 1 hour to 1 day). This permits a more reliable determination of whether stent 56 is sufficiently long to cover lesion 72.

With stent 56 in place and pressed against artery 74, balloon 58 is evacuated and device 16 is proximally withdrawn. Guidewire 32 can be withdrawn as well, or left in place to permit advancing any device contemplated for a further procedure.

Figure 9:
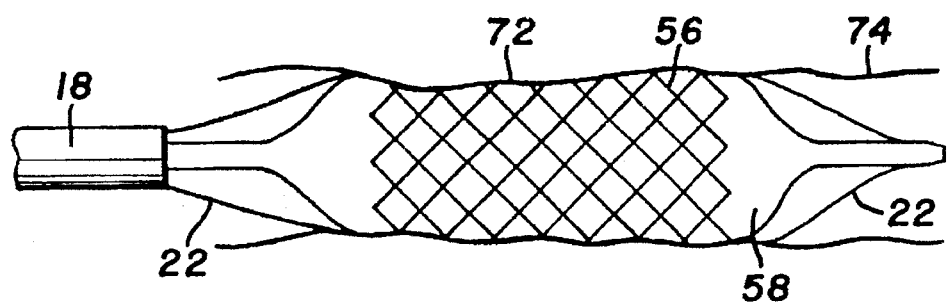

As best seen in FIGS. 8 and 9, when outer catheter 18 is retracted (i.e. moved proximally relative to inner catheter 28), it draws sheath 22 proximally as well, so that the rolling membrane eventually overlies and surrounds dilatation balloon 58. The axial length of the sheath is sufficient to provide sheath extension proximally of the dilatation balloon, so that the balloon is completely surrounded and covered. For example, the sheath axial length is sufficient if, with the sheath in the stent retaining state, the combined axial length of inner and outer sheath layers 46 and 48 exceeds the axial distance from distal end 54 to proximal neck 60.

The primary advantage of this configuration is that the rolling membrane, in addition to retaining the stent before retraction, provides a protective layer between tissue and the dilatation balloon after retraction. If the dilatation balloon were to burst during high pressure angioplasty, or if a tear or other fault allowed dilatation fluid to exit the balloon, sheath 22 would cause the dilatation fluid to flow proximally into lumen 20 of the outer catheter, thus protecting surrounding arterial tissue against exposure to exploding or jetting dilatation fluid. Also, as balloon 58 is inflated (FIG. 9), sheath 22 provides a layer between the dilatation balloon and stent 56, preventing any damage to the balloon that might result from direct contact with the stent.

The structure and material of sheath 22 will generally be chosen to provide sufficient strength to counteract the restoring force of elastically compressed stent 56 during delivery while providing sufficient elasticity so that the sheath does not unduly interfere with dilatation of balloon 58. In certain applications a recovery metal stent is advantageous. The sheath, when not required to constrain a self-expanding stent during delivery, can be substantially more elastic.

The expanded balloon acts through sheath 22 to press stent 56 radially outward and against the surrounding arterial tissue. Momentarily, this radially expands and axially shortens stent 56 beyond a state of equilibrium at which the respective restoring forces within the stent and within surrounding tissue counterbalance one another. When balloon 58 is evacuated and withdrawn, stent 56 slightly radially contracts and axially elongates to re-establish equilibrium. Thus stent 56 is caused to overexpand and then contract radially into equilibrium. As a result, the fluid flow path in the artery is smoother and flow is more laminar. With flow turbulence reduced, the potential for thrombus formation in the area of the stent likewise is reduced. The balloon expansion of the stent also enables the physician to more reliably confirm that the implanted stent has sufficient length relative to the lesion under treatment.

Following balloon evacuation, the distal region of the device reassumes the shape shown in FIG. 8, whereby the device is easily proximally withdrawn to leave the stent in place.

Figure 10:
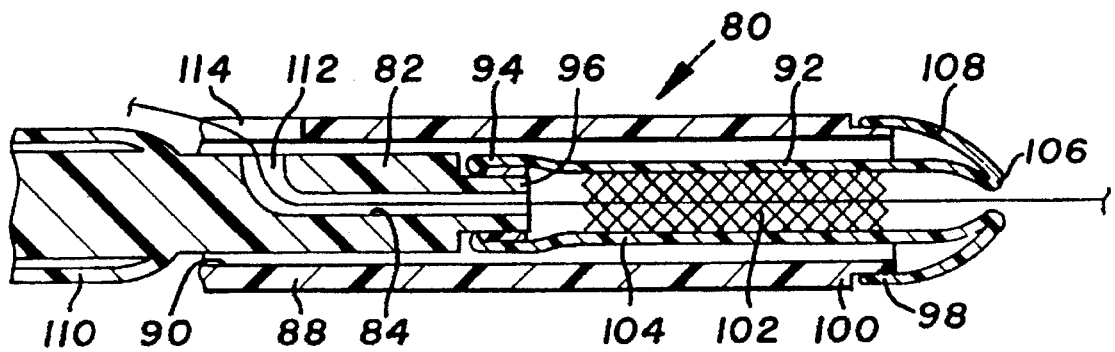
FIG. 10 is an elevation in section of a distal end region of an alternative embodiment device for deploying radially self-expanding stents.

FIG. 10 shows the distal region of an alternative stent deployment device 80. Device 80 includes an inner catheter 82 with a guidewire lumen 84 that accommodates a guidewire 86. An outer catheter 88 has a catheter lumen 90 containing the inner catheter. A tubular sheath 92 includes a first end 94 mounted to the distal end 96 of the inner catheter, and a second end 98 mounted to the distal end 100 of outer catheter 88. A radially self-expanding stent 102 extends distally of the inner catheter, maintained in an axially elongated and radially compressed state. Device 80 differs from device 16 primarily in that outer catheter 88 extends distally beyond the inner catheter along the stent, and thus cooperates with an inner sheath layer 104 to maintain the stent under radial compression. Sheath 92 is turned back upon itself to provide a distal turn 106 and a relatively short outer sheath layer 108. Outer layer 108 and inner layer 104 converge to form a tapered distal tip of the device.

A dilatation balloon 110 is mounted to inner catheter 82 near distal end 96, and expandable in the same manner as dilatation balloon 58. When retracted, outer catheter 88 is proximal of balloon 110, so that sheath 92 once again overlies and surrounds the dilatation balloon to perform its protective function. Again, the combined length of the inner and outer sheath layers, in this case primarily the length of inner layer 104, exceeds the distance from the inner catheter distal end to the balloon proximal end.

Another feature of device 80 concerns guidewire lumen 84. The guidewire lumen does not run the length of inner catheter 82 as before, but ends just proximally of dilatation balloon 110. An aperture 112 through the catheter, open to lumen 84, allows guidewire 86 to exit the inner catheter. An elongate slit 114 through outer catheter 88 runs axially along the outer catheter and allows the guidewire to exit deployment device 80. When the device is in the stent retaining state, aperture 112 of the inner catheter is axially aligned with the distal end of slit 114. This feature is advantageous for procedures that require shorter guidewires or one or more guidewire exchanges, as is explained in the aforementioned PCT application, Publication No. WO 94/15549.

Figure 11:
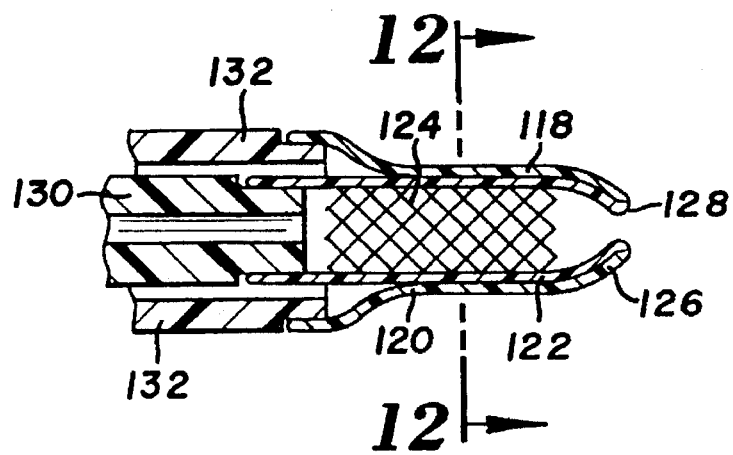
FIG. 11 is an elevational view of a distal region of another alternative embodiment deployment device.
Figure 12:
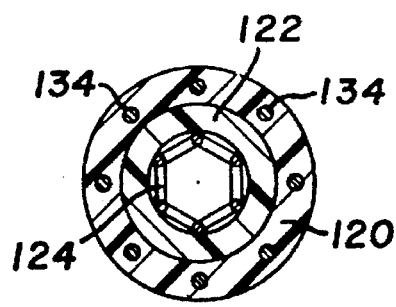
FIG. 12 is a sectional view taken along the line 12—12 in FIG. 11.

FIGS. 11 and 12 illustrate a stent retaining sheath 118 formed according to a further alternative embodiment of the invention. Sheath 118 is doubled over upon itself to provide inner and outer sheath layers 120 and 122 that surround a radially self-expanding stent 124, to maintain the stent in a radially compressed, axially elongated state against a restoring force. The distal portions of sheath layers 120 and 122 converge to provide a tapered distal tip 126 that terminates at a distal end 128. The proximal end of the inner sheath layer is mounted to an inner catheter 130, while the proximal end of outer layer 122 is attached to an outer catheter 132. As before, outer layer 122 is movable proximally to roll sheath 118 from its surrounding relation to the stent, whereby the stent progressively radially self-expands.

Several filaments 134 are embedded into sheath 118 and extend axially along outer sheath layer 122. Filaments 134 preferably are formed of a high modulus of elasticity fiber such as that sold under the brand name Kevlar, or Dacron fibers. Filaments 134 lend rigidity in the axial direction, for improved "pushability" of the device through arterial and other passageways.

Figure 13:
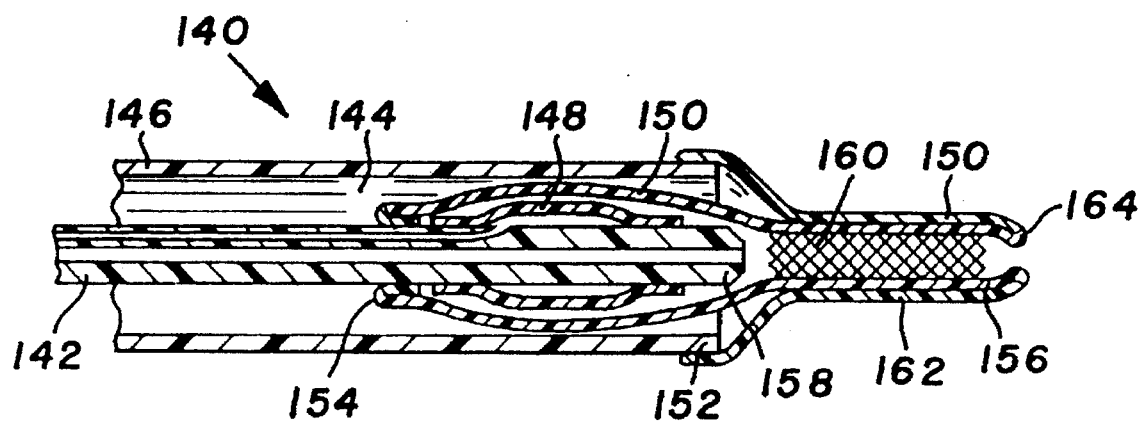
FIGS. 13 and 14 illustrate the distal end portion of a further alternative embodiment device.
Figure 14:
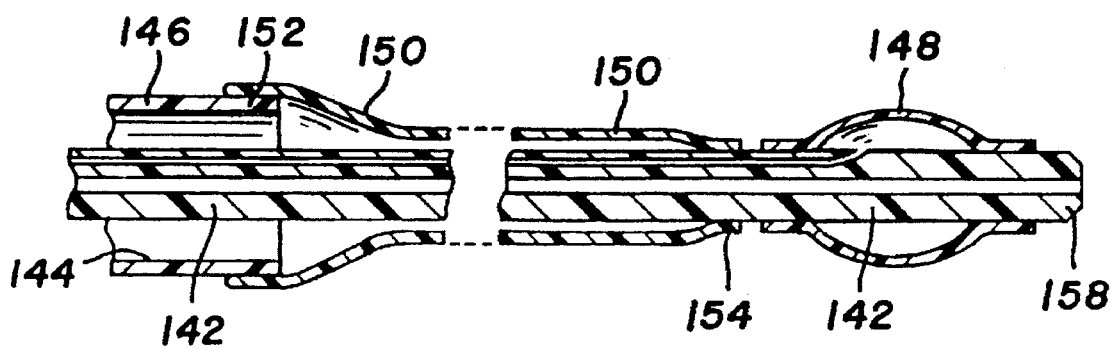

FIGS. 13 and 14 illustrate a further embodiment device 140 in which an inner balloon catheter 142 is contained within a lumen 144 of an outer catheter 146. Balloon catheter 142 includes a lumen for a guidewire. A dilatation balloon 148 is mounted to catheter 142 near its distal end, and is in fluid communication with a balloon dilatation lumen of the catheter, through which a fluid under pressure can be supplied to the balloon to expand the balloon.

A tubular sheath 150 is fixed at one end to a distal end 152 of the outer catheter. The opposite end of the sheath is fixed to balloon catheter 142, but not at its distal end. Rather, the sheath is fixed at a location proximal relative to balloon 148, as indicated at 154. Consequently a substantial portion of a sheath inner layer 156 surrounds the balloon. A distal portion of the inner layer extends beyond distal end 158 of the inner catheter, to surround and contain a stent 160 in a radially reduced delivery state as described in connection with device 16. Likewise, the sheath includes an outer sheath layer 162, and the sheath is modified to form a distal tip 164 in the manner previously explained.

Proximal movement of outer catheter 146, relative to balloon catheter 142, rolls sheath 150 in the proximal direction to release stent 160. As seen in FIG. 14, retraction of the sheath leaves dilatation balloon 148 exposed, rather than surrounded by the sheath as in the first embodiment. The primary advantage of this embodiment (FIGS. 13 and 14) is that sheath 150 can have a relatively high elastic modulus for confining a radially self-expanding stent having a higher spring constant. The sheath need not have sufficient elasticity to accommodate dilatation balloon expansion in this embodiment. In certain applications, this advantage outweighs the loss of the sheath as a surrounding, protective layer over the dilatation balloon.

If desired, sheaths 92, 118 and 150 can incorporate a controlled narrowing of the sheath layers near the distal tip, as explained above in connection with FIG. 5, to reduce the risk of damage to tissue during advancement of the device to the intended treatment site. The sheaths surround their respective stents and maintain the stents radially compressed, while in each case deriving added axial stiffness from the stent restoring force. The stents are maintained distally of their respective inner catheters, resulting in smaller diameter devices able to enter narrower arterial passages. In addition to their smaller diameters, the resulting devices exhibit improved pushing and tracking characteristics. If desired, axial stiffness can be enhanced by a distal extension of the outer catheter, or by axial filaments embedded into the sheath. After release of the stent at the treatment site, the retracted sheath can surround the dilatation balloon to provide an added protective layer useful in high pressure angioplasty. Alternatively, the sheath can be attached at a point where it exposes the dilatation balloon when retracted.

The preceding detailed description and drawings illustrate and explain several preferred embodiments and are not to be construed as limiting the scope of the present invention.

What is claimed is:

1. A device for deploying an expandable stent at a treatment site within a body; comprising:

a first catheter having a proximal end region and a distal end region;

a stent retaining member disposed at the distal end region of the first catheter and including an inner layer extending distally beyond the first catheter, said member being turned back upon itself to form an outer layer extending toward the first catheter, said inner layer adapted to retain an expandable stent in a reduced state along an axial length of the stent with the stent located distally of the first catheter; and a moving means operable to displace the outer layer relative to the first catheter, thereby to displace the inner layer remove the member from its retaining relation to the stent, thus to release the stent for expansion at the treatment site;

wherein a distal end of the first catheter is positioned near a proximal end of the stent when the inner layer of the stent retaining member retains the stent, to abut the stent and thereby prevent any substantial proximal migration of the stent as the retaining member is removed.

2. The device of claim 1 wherein:

said member is a sheath adapted for surrounding a radially self-expanding stent and maintaining the stent in a radially compressed state when surrounding the stent, and further adapted to allow the stent to progressively radially self-expand as the sheath is removed from its surrounding relation to the stent.

3. The device of claim 2 wherein:

the first catheter further includes a catheter wall that defines a guide wire lumen open to the distal end, and the sheath when in the retaining state defines a distal extension of the guidewire lumen.

4. The device of claim 3 further including:

an opening through the catheter wall near the distal end, for admitting a guidewire into the guidewire lumen to run distally along said distal extension of the guidewire lumen.

5. The device of claim 2 wherein:

said sheath comprises a rolling membrane, and said inner layer and outer layer are tubular.

6. The device of claim 5 wherein:

said inner layer and outer layer, when the rolling membrane is in the stent retaining state, converge in the distal direction along respective distal layer regions to form in the rolling membrane a tapered distal tip.

7. The device of claim 1 further including:

a stiffening means, extending axially at least along the outer layer, for enhancing axial rigidity of the member.

8. The device of claim 1 wherein:

said moving means include a second catheter having a second catheter lumen along substantially the entire length thereof, and wherein the first catheter is contained within the second catheter lumen.

9. The device of claim 8 wherein:

said inner layer and outer layer of the stent retaining member are formed of a fluid tight tubular rolling membrane connected to the first and second catheters in fluid tight fashion, to enable introduction of a fluid via the second catheter lumen into an area between the inner and outer layers.

10. The device of claim 9 further including:

a micropore through said outer layer to permit release of a fluid from said region into the body.

11. The device of claim 1 further including:

a dilatation balloon mounted to the first catheter along the distal end region, and a balloon dilatation lumen extending along the first catheter, said balloon dilatation lumen being open to an interior of the dilatation balloon.

12. The device of claim 11 wherein:

the member is mounted to the first catheter at a location distally of the dilatation balloon; and the combined axial length of the inner and outer layers exceeds an axial distance from said location to a proximal end of the dilatation balloon.

13. The device of claim 11 wherein:

said member is mounted to the first catheter at a location proximally of the dilatation balloon.

14. An apparatus including a radially expandable stent and a device for deploying the radially expandable stent at a treatment site within a body lumen; comprising:

a radially expandable stent;

an elongate first catheter having a proximal end and a distal end;

an elongate second catheter having a proximal end and a distal end, and a catheter lumen running along the second catheter and open to the distal end of the second catheter, wherein the first catheter is contained within the catheter lumen; and a tubular, pliable and flexible sheath, and means for connecting a first end of the sheath to the first catheter, and for connecting a second end of the sheath to a distal end of the second catheter;

wherein the first catheter and the second catheter are movable relative to one another to position the sheath in a stent retaining state in which the sheath surrounds the radially expandable stent along an axial length of the stent, the entire stent is disposed distally of the distal end of the first catheter, and the stent is in a radially reduced state to facilitate use of the first and second catheters to deliver the stent to a treatment site within a body lumen; and wherein the first catheter and the second catheter are further moveable relative to one another to roll the sheath proximally from its surrounding relation to the stent, thus to release the stent for radial expansion at the treatment site.

15. The apparatus of claim 14 wherein:

said sheath is adapted to confine the radially self-expanding stent in a radially compressed state when surrounding the stent, and to allow the stent to radially self-expand as the sheath is rolled proximally from the stent.

16. The apparatus of claim 14 wherein:

said sheath, when in the stent retaining state, includes an inner sheath layer extended distally from the distal end of the first catheter, and is turned back upon itself to provide an outer sheath layer extended proximally to the distal end of the second catheter and surround the inner sheath layer.

17. The apparatus of claim 16 wherein:

the connections of the sheath with the respective distal ends of the first and second catheters are fluid tight, to facilitate introduction of a fluid to a location between the inner sheath layer and the outer sheath layer, via the catheter lumen.

18. The apparatus of claim 17 further including:

a micropore through the sheath outer layer, for releasing fluids from said location into the body cavity.

19. The apparatus of claim 16 further including:

an axially extended stiffening means for enhancing the axial rigidity of the sheath, at least along the outer sheath layer.

20. The apparatus of claim 14 further including:

a flexible dilatation balloon mounted to the first catheter near the distal end of the first catheter, and a balloon inflation lumen extending along the first catheter, said balloon inflation lumen being open to an interior of the dilatation balloon.

21. The apparatus of claim 20 wherein:

the sheath is connected to a distal end of the first catheter; and an axial length of the sheath, between the first and second ends, exceeds an axial distance from the distal end of the first catheter to a proximal end of the dilatation balloon.

22. The apparatus of claim 20 wherein:

the sheath is connected to the first catheter at a location proximally of the dilatation balloon.

23. An apparatus for deploying a radially expandable stent at a treatment site within a body lumen and for forcing the stent against the body lumen after deployment; said apparatus comprising:

an elongate balloon catheter having a proximal end and a distal end;

a stent releasing means disposed along the balloon catheter and having a proximal end;

a sheath, and means for connecting a first end of the sheath to the balloon catheter and connecting a second end of the sheath to the stent releasing means; and a flexible dilatation balloon mounted to the balloon catheter near said distal end of the balloon catheter, and a balloon inflation lumen along the balloon catheter for supplying a fluid under pressure to the dilatation balloon;

wherein the sheath is positionable in a stent retaining state with the sheath surrounding and engaging a radially expandable stent along an axial length of the stent when at least a portion of the stent extends distally of said balloon catheter, thus to maintain the stent in a radially reduced state to facilitate use of the balloon catheter to deliver the stent to a treatment site within a body lumen;

wherein the stent releasing means is movable proximally relative to the balloon catheter to roll the sheath away from its surrounding relation to the stent, thus to release the stent for radial expansion at the treatment site; and wherein the first end of the sheath is connected to the balloon catheter at a location distally of the dilatation balloon.

24. The apparatus of claim 23 wherein:

an axial length of the sheath from its first end to its second end exceeds an axial distance from the first end of the sheath to a proximal end of the dilatation balloon.

25. The apparatus of claim 23 wherein:

said first end of the sheath is connected to the catheter at a location proximally of the dilatation balloon.

26. The apparatus of claim 23 wherein:

said sheath is adapted to maintain a radially self-expanding stent in a radially compressed state when surrounding the stent, and to allow the stent to radially self-expand as the sheath is rolled away from the stent.

27. The apparatus of claim 23 wherein:

said stent releasing means includes a release catheter having a catheter lumen along substantially the entire length thereof, and wherein the balloon catheter is contained within the catheter lumen.

28. The apparatus of claim 27 wherein:

the second end of the sheath is mounted to a distal end of the release catheter.

29. The apparatus of claim 23 wherein:

said sheath, when in the stent retaining state, includes an inner layer extended along and engaging the stent, and is turned back upon itself to provide an outer layer extended along and surrounding the inner layer.

30. The apparatus of claim 29 wherein:
the sheath and the connecting means are fluid tight, to facilitate introduction of a fluid via the catheter lumen to a location between the inner sheath layer and the outer sheath layer.

31. The apparatus of claim 23 wherein:
the first end of the sheath is mounted to the balloon catheter at said distal end of the balloon catheter, and the stent when maintained in the radially reduced state is located entirely distally of said distal end of the balloon catheter.

32. A device for releasably securing a radially expandable stent near a distal end of an elongate catheter, said device comprising:
a stent retaining sheath mounted to a distal end region of a catheter, said sheath being positionable in a stent retaining state in which the sheath surrounds and engages a radially expandable stent along an axial length of the stent, thus to maintain the stent in a radially reduced state with the stent located distally of the catheter, to facilitate use of the catheter for delivery of the stent to a treatment site within a body lumen;
wherein the sheath is movable proximally relative to the catheter to allow a rolling of the sheath away from its surrounding relation to the stent, to release the stent for radial expansion at the treatment site;
wherein said distal end region is disposed near a proximal end of the stent when the sheath maintains the stent, to abut the stent and thereby prevent any substantial proximal migration of the stent as the sheath is rolled away to release the stent.

33. The device of claim 32 wherein:
the sheath when surrounding the stent includes an inner sheath layer surrounding and engaging the stent, and is turned back upon itself to provide an outer sheath layer surrounding the inner sheath layer; and
said rolling is accomplished by moving the outer sheath layer proximally relative to the stent.

34. The device of claim 33 wherein:
said radially expandable stent is radially self-expanding, and the inner sheath layer surrounds the radially self-expanding stent and maintains the stent in a radially compressed state and, when progressively rolled away from its surrounding relation to the stent, releases the stent for radial self-expansion.

35. The device of claim 33 wherein:
said sheath comprises a rolling membrane, and said inner sheath layer and outer sheath layer are tubular; and
said inner sheath layer and outer sheath layer, when the rolling membrane is in the stent retaining state, converge in the distal direction along respective sheath layer regions to form in the rolling membrane a tapered distal tip.

36. The device of claim 32 further including:
a stiffening means extending axially along the sheath for enhancing axial rigidity.

37. The device of claim 33 further including:
a stent releasing means attached to the outer sheath layer and operable from a proximal end of the catheter to move the outer sheath layer proximally relative to the catheter.

38. The device of claim 33 wherein:
the sheath is fluid tight to facilitate introduction of a fluid into a region between the inner and outer sheath layers.

39. A device for deploying a radially expandable stent at a treatment site within a body lumen, comprising:

an elongate delivery catheter having a proximal end region and a distal end region;
a tubular stent retaining sheath mounted to a distal end region of the delivery catheter and extended distally from the delivery catheter whereby the sheath is adapted to surround a radially expandable stent along an axial length of the stent, to maintain the stent in a radially reduced state to facilitate use of the delivery catheter to deliver the stent to a treatment site within a body lumen, said sheath, distally of the stent, converging in the distal direction to form a tapered distal tip; and
a stent releasing means operatively coupled to the sheath and movable relative to the delivery catheter to roll the sheath away from its surrounding relation to the stent, to release the stent for radial expansion at the treatment site;
wherein said sheath, when so maintaining the stent, includes an inner sheath layer extended distally from the delivery catheter and engaging the stent, and further is turned back upon itself at said distal tip to provide an outer sheath layer extended proximally toward the delivery catheter and surrounding the inner sheath layer; and
wherein said inner sheath layer and said outer sheath layer, in the region of the distal tip, provide a transition region over which the hardness of the sheath diminishes in the distal direction, whereby said distal tip is softer than the remainder of the sheath.

40. The device of claim 39 wherein:
the outer sheath layer and the inner sheath layer, in the region of said distal tip, are progressively narrowed in the distal direction whereby the thickness of said distal tip diminishes in said distal direction.

41. The device of claim 39 wherein:
a distal end of the delivery catheter is near a proximal end of the stent when the stent is surrounded by the sheath, to prevent any substantial travel of the stent, proximally relative to the delivery catheter and sheath, when surrounded by the sheath.

42. The device of claim 40 wherein:
said stent releasing means includes a release catheter surrounding the delivery catheter and coupled at its distal end to the outer sheath layer, and movable proximally relative to the delivery catheter to move the outer sheath layer proximally, thus to roll the sheath away from the stent.

43. A device for deploying an expandable stent at a treatment site within a body, comprising:
a first catheter having a proximal end region and a distal end region;
a dilatation means mounted to the first catheter along the distal end region of the first catheter;
a stent retaining member disposed at the distal end region of the first catheter and including an inner layer extending distally beyond the first catheter, said member being turned back upon itself to form an outer layer toward the first catheter, said inner layer adapted to retain an expandable stent in a reduced state along an axial length of the stent with the stent located distally of the first catheter, wherein the stent retaining member is mounted to the first catheter at a location distally of the dilatation means; and
a moving means operable to displace the outer catheter relative to the first catheter, thereby to displace the inner layer to remove the member from its retaining relation to the stent, thus to release the stent for expansion at the treatment site.

44. The device of claim 43 wherein:

said dilatation means comprises a dilatation balloon, and the first catheter includes a balloon dilatation lumen open to an interior of the dilatation balloon.

45. The device of claim 44 wherein:

the combined axial length of the inner and outer layers exceeds an axial distance from said location to a proximal end of the dilatation balloon.

46. The device of claim 43 wherein:

a distal end of the first catheter is positioned near a proximal end of the stent when the stent retaining member retains the stent, to abut the stent and thereby prevent any substantial proximal migration of the stent as the member is removed.

47. The device of claim 43 wherein:

said stent retaining member is a sheath adapted for surrounding a radially self-expanding stent and maintaining the stent in a radially compressed state when surrounding the stent, and further adapted to allow the stent to progressively, radially self-expand as the sheath is removed from its surrounding relation to the stent.

48. The device of claim 47 wherein:

said sheath comprises a rolling membrane, and said inner layer and outer layer are tubular.

49. The device of claim 48 wherein:

said inner layer and outer layer, when the rolling member is in the stent retaining state, converge in the distal direction along respective distal layer regions to form in the rolling membrane a tapered distal tip.

50. The device of claim 43 further including:

a stiffening means extending axially at least along the outer layer, for enhancing axial rigidity of the stent retaining member.

51. The device of claim 43 wherein:

said moving means include a second catheter having a catheter lumen for containing the first catheter.

52. The device of claim 51 wherein:

said inner layer and outer layer of the stent retaining member are formed of a substantially fluid tight tubular rolling membrane connected to the first and second catheters in fluid tight fashion, to enable introduction of a fluid via the second catheter lumen into an area between the inner and outer layers.

53. A device for deploying an expandable stent at the treatment site within a body; comprising:

a first catheter having a proximal end and a distal end;

a stent retaining member mounted to the first catheter and extending distally beyond said distal end of the first catheter to provide an inner layer, said stent retaining member further being turned back upon itself to form an outer layer adjacent and outside of the inner layer and extending proximally toward the first catheter, said inner layer adapted to retain an expandable stent in a reduced radius state along an axial length of the stent with the entire stent disposed distally of said distal end of the first catheter; and a moving means disposed outside of the first catheter and coupled to the outer layer of the stent retaining member, said moving means being operable to displace the outer layer relative to the first catheter, thereby to displace the inner layer to remove the inner layer from its retaining relation to the stent, thus to release the stent for expansion at the treatment site.

54. The device of claim 53 wherein:

said distal end of the first catheter is positioned near a proximal end of the stent when the inner layer of the stent retaining member retains the stent, to abut the stent and thereby prevent any substantial proximal migration of the stent as the inner layer of the retaining member is removed.

* * * * *

UNITED STATES PATENT AND TRADEMARK OFFICE
CERTIFICATE OF CORRECTION

PATENT NO. : 5,662,703

DATED : September 2, 1997

INVENTOR(S) : Yurek et al.

It is certified that error appears in the above-identified patent and that said Letters Patent is hereby corrected as shown below:

Column 10, line 3, after "layer" insert -- to --.
Column 11, line 44, change "surround" to -- surrounding --.

Signed and Sealed this

Fourth Day of November, 1997

Attest:

BRUCE LEHMAN

Attesting Officer

Commissioner of Patents and Trademarks